(12) United States Patent
Yada et al.

(10) Patent No.: US 8,652,519 B2
(45) Date of Patent: Feb. 18, 2014

(54) DISSOLUTION PROPERTIES OF DRUG PRODUCTS CONTAINING OLMESARTAN MEDOXOMIL

(75) Inventors: Shuichi Yada, Kanagawa (JP); Hideki Yano, Kanagawa (JP); Tsuyoshi Nagaike, Kanagawa (JP); Misato Yokoi, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/299,221

(22) Filed: Nov. 17, 2011

(65) Prior Publication Data

US 2012/0064158 A1    Mar. 15, 2012

Related U.S. Application Data

(62) Division of application No. 12/921,627, filed as application No. PCT/JP2009/053859 on Mar. 2, 2009, now abandoned.

(30) Foreign Application Priority Data

Mar. 13, 2008    (JP) ................. 2008-064500

(51) Int. Cl.
| | | |
|---|---|---|
| *A61K 31/455* | (2006.01) | |
| *A61K 9/30* | (2006.01) | |
| *A61K 31/549* | (2006.01) | |
| *A61K 9/36* | (2006.01) | |

(52) U.S. Cl.
USPC ......... 424/465; 424/400; 514/356; 514/223.5

(58) Field of Classification Search
USPC ................. 424/400, 465; 514/356, 223.5
See application file for complete search history.

(56) References Cited

U.S. PATENT DOCUMENTS

| | | | |
|---|---|---|---|
| 3,025,292 A | 3/1962 | Jones et al. | |
| 4,572,909 A | 2/1986 | Campbell et al. | |
| 5,616,599 A | 4/1997 | Yanagisawa et al. | |
| 2006/0281795 A1 * | 12/2006 | Kuroita et al. | 514/364 |
| 2008/0279942 A1 | 11/2008 | Hamaura et al. | |
| 2010/0237530 A1 | 9/2010 | Yada et al. | |

FOREIGN PATENT DOCUMENTS

| | | | | |
|---|---|---|---|---|
| WO | WO 02/41890 A1 | 5/2002 | | |
| WO | WO 2004/010976 A1 | 2/2004 | | |
| WO | WO 2004/067003 A1 | 8/2004 | | |
| WO | WO 2006/029057 A1 | 3/2006 | | |
| WO | WO 2007/001065 | * | 1/2007 | ............... A61K 9/16 |
| WO | WO 2007/001065 A2 | 1/2007 | | |
| WO | WO 2007/001067 A2 | 1/2007 | | |
| WO | WO 2008/001734 A1 | 1/2008 | | |
| WO | WO 2008/032107 A1 | 3/2008 | | |

OTHER PUBLICATIONS

K-Tron. Continous Pharmaceutical Dry Dranulation and Direct Compression Tableting Process (2006).*
J.M. Neutel et al, Effects of a structured treatment algorithm on blood pressure goal rates in both stage 1 and stage 2 hypertension, Journal of Human Hypertension, Apr. 2006, vol. 20, No. 4, pp. 255-262.
Extended European Search Report (6 pages) dated Jan. 25, 2011 in the corresponding EP application 09 71 9057.3.
U.S. Appl. No. 12/305,705, filed Feb. 4, 2009.
U.S. Appl. No. 13/135,961, filed Jul. 19, 2011.
European Official Action mailed Oct. 28, 2013, which issued in the counterpart European Patent Application No. 09719057.3-1464.

* cited by examiner

*Primary Examiner* — Anoop Singh
*Assistant Examiner* — Anna Falkowitz
(74) *Attorney, Agent, or Firm* — Holtz Holtz Goodman & Chick PC

(57) ABSTRACT

A pharmaceutical tablet containing olmesartan medoxomil and amlodipine besylate, which has improved dissolvability. Said composition contains (A) olmesartan medoxomil and (B) amlodipine besylate as active ingredients and (C) a calcium-containing additive. A method of improving the dissolution properties of a pharmaceutical composition containing olmesartan medoxomil and amlodipine besylate by using said composition is also provided.

8 Claims, No Drawings

DISSOLUTION PROPERTIES OF DRUG PRODUCTS CONTAINING OLMESARTAN MEDOXOMIL

CROSS-REFERENCE TO RELATED APPLICATIONS

This application is a divisional application of Ser. No. 12/921,627 filed Sep. 9, 2010 (abandoned) which is the United Stated national phase application of International Application PCT/JP2009/053859 filed Mar. 2, 2009.

TECHNICAL FIELD

The present invention relates to a pharmaceutical composition containing olmesartan medoxomil and amlodipine.

BACKGROUND ART

Angiotensin II receptor antagonists and calcium channel antagonists are presently widely used as drugs to treat or prevent hypertension, heart disease, or the like. Angiotensin II receptor antagonists, which are renin-angiotensin inhibitors, are particularly effective against renin-dependent hypertension, and they demonstrate a protective action against cardiovascular or renal damage. Calcium channel antagonists have a natriuretic action in addition to a vasodilating action, and they are also effective against body fluid retention (renin-independent) hypertension. It is therefore expected that the combined use of an angiotensin II receptor antagonist and a calcium channel antagonist would yield a calcium channel antagonist action and a secondary natriuretic action in vascular smooth muscles due to the calcium channel antagonist in addition to the inhibitory effect on the renin-angiotensin system due to the angiotensin II receptor antagonist, which would make it possible to inhibit multiple hypertension factors simultaneously, and that this combination would demonstrate stable and sufficient therapeutic or preventative effects against hypertension, regardless of the cause of the disease.

Thiazide diuretics are also widely used as drugs to treat or prevent hypertension, heart disease, or the like. Their diuretic effect makes thiazide diuretics effective for the treatment of hypertension. It is therefore expected that the combined use of an angiotensin II receptor antagonist and a thiazide diuretic would make it possible to inhibit multiple hypertension factors simultaneously due to the diuretic action of the thiazide diuretic in addition to the inhibitory effect on the renin-angiotensin system due to the angiotensin II receptor antagonist, and that this combination would demonstrate stable and sufficient therapeutic or preventative effects against hypertension, regardless of the cause of the disease.

(5-Methyl-2-oxo-1,3-dioxolan-4-yl)methyl 4-(1-hydroxy-1-methylethyl)-2-propyl-1-[2'-(1H-tetrazol-5-yl)biphenyl-4-ylmethyl]imidazole-5-carboxylate (called olmesartan medoxomil hereinafter) is an excellent angiotensin II receptor antagonist, and its usefulness as a drug for treating or preventing hypertension, heart disease, and the like is well known (Japanese Patent 2082519, U.S. Pat. No. 5,616,599).

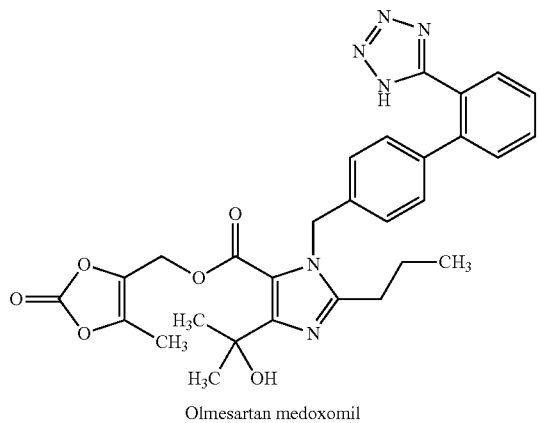 [SMILES: CCCc1nc(C(C)(C)O)c(C(=O)OCc2oc(=O)oc2C)n1Cc1ccc(-c2ccccc2-c2nnn[nH]2)cc1]

Olmesartan medoxomil

Olmesartan medoxomil is marketed as Olmetec (registered trademark) tablets or Benicar®, and these contain 5 mg, 10 mg, 20 mg, or 40 mg of olmesartan medoxomil as active ingredient and low-substituted hydroxypropyl cellulose, hydroxypropyl cellulose, microcrystalline cellulose, lactose, and magnesium stearate as excipients.

3-Ethyl-5-methyl-(±)-2-[(2-aminoethoxy)methyl]-4-(2-chlorophenyl)-1,4-dihydro-6-methylpyridine-3,5-dicarboxylate (called amlodipine hereinafter) is a well-known compound which is an excellent calcium channel antagonist and is useful as a drug for treating or preventing hypertension, heart disease, and the like.

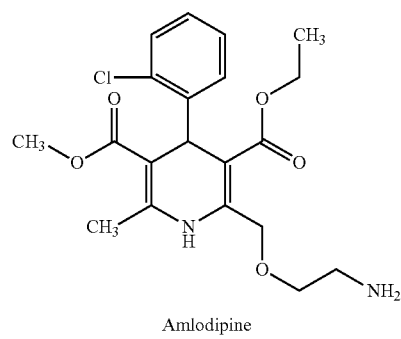 [SMILES: CCOC(=O)C1=C(COCCN)NC(C)=C(C(=O)OC)C1c1ccccc1Cl]

Amlodipine

Amlodipine is marketed as Norvasc (registered trademark) tablets, and it contains 3.47 mg or 6.93 mg of amlodipine besylate as active ingredient (2.5 mg or 5 mg of amlodipine) and microcrystalline cellulose, anhydrous calcium hydrogen phosphate, carboxymethyl starch sodium, magnesium stearate, hypromellose, titanium oxide, talc, and carnauba wax as excipients.

Further, 6-chloro-3,4-dihydro-2H-1,2,4-benzothiadiazine-7-sulfonamide-1,1-dioxide (called hydrochlorothiazide hereinafter) is a compound that is well known as an excellent thiazide diuretic, and it is described, for example, in U.S. Pat. No. 3,025,292.

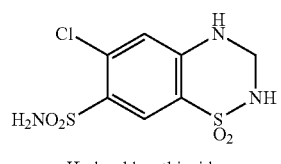

Hydrochlorothiazide

Drugs which combine olmesartan medoxomil and amlodipine (pamphlet of International Patent Publication WO 2004/067003) and drugs which combine olmesartan medoxomil and hydrochlorothiazide (pamphlet of International Patent Publication WO 2002/041890) are known in the prior art, but there is no known solid dosage form such as that of the present invention containing olmesartan medoxomil and amlodipine having improved dissolution properties as a result of the further inclusion of excipients containing calcium. Moreover, there is no known solid dosage form such as that of the present invention containing olmesartan medoxomil, amlodipine and hydrochlorothiazide having improved dissolution properties as a result of the further inclusion of excipients containing calcium.

[Patent Document 1] Japanese Patent 2082519 (U.S. Pat. No. 5,616,599)
[Patent Document 2] Japanese Patent 1401088 (U.S. Pat. No. 4,572,909)
[Patent Document 3] U.S. Pat. No. 3,025,292
[Patent Document 4] Pamphlet of International Patent Publication WO 2004/067003
[Patent Document 5] Pamphlet of International Patent Publication WO 2002/041890

DISCLOSURE OF THE INVENTION

Problem to be Solved by the Invention

The problem of the present invention is to provide a pharmaceutical composition with improved dissolution properties containing (A) olmesartan medoxomil and (B) amlodipine as active ingredients and (C) a calcium-containing excipient.

In recent years, hypertension patients have tended to use multiple hypotensive drugs with different action mechanisms in combination in order to achieve reliable blood pressure control. Of these, olmesartan medoxomil, which is an angiotensin II receptor antagonist, and amlodipine, which is a calcium channel antagonist, have been widely used in combination in the medical field as a combination which promises reliable therapeutic effects against hypertension. However, it was discovered that the dissolution properties of olmesartan medoxomil are diminished by interactions between these drugs when they are blended.

Means for Solving the Problem

As a result of conducting dedicated research in order to solve the problem described above, the present inventors discovered that a pharmaceutical composition with improved dissolution properties can be obtained by including a calcium-containing excipient, and they thereby completed the present invention.

The present invention provides a pharmaceutical composition (in particular, a composition for preventing or treating hypertension) containing (A) olmesartan medoxomil and (B) amlodipine as active ingredients and (C) a calcium-containing excipient; a method of using olmesartan medoxomil and amlodipine to produce the pharmaceutical composition described above (in particular, a composition for preventing or treating hypertension); a method of preventing or treating diseases (hypertension, in particular) by administering the above pharmaceutical composition containing pharmacologically effective doses of olmesartan medoxomil and amlodipine to warm-blooded animals (humans, in particular); and a method of improving the dissolution properties of a pharmaceutical composition (in particular, a composition for treating or preventing hypertension) containing olmesartan medoxomil and amlodipine by including a calcium-containing excipient. In addition, the pharmaceutical composition described above may also include hydrochlorothiazide as an active ingredient.

In other words, the present invention provides:
(1) a pharmaceutical composition containing (A) olmesartan medoxomil and (B) amlodipine as active ingredients and (C) a calcium-containing excipient;
(2) a pharmaceutical composition according to (1), wherein component (C) is one or more types of compounds selected from carmellose calcium, calcium silicate, calcium hydrogen phosphate, calcium carbonate, calcium sulfate dihydrate, calcium ascorbate, calcium chloride, and calcium stearate;
(3) a pharmaceutical composition according to (1), wherein component (C) is carmellose calcium;
(4) a pharmaceutical composition according to any of (1)-(3), wherein the pharmaceutical composition is formulated as a single formulation;
(5) a pharmaceutical composition according to (4), wherein the drug product is a solid dosage form;
(6) a pharmaceutical composition according to (4), wherein the drug product is a powder, fine granules, a granule, a capsule, or a tablet;
(7) a pharmaceutical composition according to (4), wherein the drug product is a tablet;
(8) a pharmaceutical composition according to any of (1)-(7) which is coated;
(9) a pharmaceutical composition according to (8), wherein component (C) is included in the coating;
(10) a pharmaceutical composition according to any of (1)-(9) which further includes hydrochlorothiazide as an active ingredient;
(11) a pharmaceutical composition according to any of (1)-(10) for treating or preventing hypertension;
(12) a method of improving the dissolution properties of olmesartan medoxomil using a pharmaceutical composition according to any of (1)-(11).

Effect of the Invention

With the present invention, it is possible to provide a pharmaceutical composition with improved dissolution properties containing (A) olmesartan medoxomil, (B) amlodipine, and (C) a calcium-containing excipient.

BEST MODE FOR CARRYING OUT THE INVENTION

The active ingredients of the pharmaceutical composition of the present invention are olmesartan medoxomil and amlodipine. Hydrochlorothiazide may also be added as an active ingredient of the pharmaceutical composition of the present invention.

Olmesartan medoxomil, which is one of the active ingredients of the pharmaceutical composition of the present invention, can easily be manufactured in accordance with the method described in Japanese Patent 2082519 (U.S. Pat. No. 5,616,599) or the like.

Amlodipine, which is another active ingredient of the pharmaceutical composition of the present invention, can easily be manufactured in accordance with the method described in Japanese Patent 1401088 (U.S. Pat. No. 4,572,909) or the like. Amlodipine can form pharmacologically acceptable salts, and these salts are also included in the present invention. The pharmacologically acceptable salts may be either acid-addition salts or base-addition salts. Examples include besylate, hydrochlorides, hydrobromides, fumarates, citrates, tartrates, maleates, camsilates, lactates, mesylates, nicotinates, and gluconates, and although the present invention is not limited to these, besylates are preferred.

Hydrochlorothiazide, which is another active ingredient of the pharmaceutical composition of the present invention, can easily be manufactured in accordance with the method described in U.S. Pat. No. 3,025,292. Hydrochlorothiazide includes pharmacologically acceptable salts, examples of which include hydrohalic acid salts such as hydrofluorides, hydrochlorides, hydrobromides, and hydriodides; nitrates; perchlorates; sulfates; phosphates; C1-C4 alkane sulfonates which may be substituted with halogens such as methanesulfonates, trifluoromethanesulfonates, and ethanesulfonates; C6-C10 arylsulfonates which may be substituted with C1-C4 alkyls such as benzenesulfonates and p-toluenesulfonates; C1-C6 fatty acid salts such as acetates, malates, fumarates, succinates, citrates, tartrates, oxalates, and maleates; or amino acid salts such as glycine salts, lysine salts, arginine salts, ornithine salts, glutamic acid salts, and aspartic acid salts. Hydrochlorides, nitrates, sulfonates, or phosphates are preferred, and hydrochlorides are particularly preferred.

There are no restrictions regarding the "calcium-containing excipient" in the pharmaceutical composition of the present invention as long as it is a pharmacologically acceptable excipient containing calcium, and calcium may be included in any excipient such as a filler, a lubricant, a binder, a disintegrant, an emulsifying agent, a stabilizer, a sweetening or flavoring agent, or a diluent. Examples include carmellose calcium (made by Gotoku Chemical Co., Ltd., ECG-505 or the like), calcium silicate, calcium hydrogen phosphate, calcium carbonate, calcium sulfate dihydrate, calcium ascorbate, calcium chloride, and calcium stearate, and carmellose calcium is preferred. In the present invention, these can be used alone, or two or more types can be used in combination. There are no particular restrictions regarding the amount of calcium present in the pharmaceutical composition, but it is preferably at least 0.08% of the formula weight, more preferably within the range of 0.08-30 weight %, even more preferably within the range of 0.08-4 weight %, and most preferably within the range of 0.2-4 weight %. The calcium-containing excipient may be contained uniformly throughout the entire drug product or in a specific part of the drug product. If a film coating layer is provided, the calcium-containing excipient may be included in the film coating layer.

The pharmaceutical composition of the present invention may further contain additional appropriate pharmaceutically acceptable excipients such as fillers, lubricants, binders, disintegrants, emulsifying agents, stabilizers, sweetening and flavoring agents, or diluents as necessary.

Examples of "fillers" that may be used include organic fillers including sugar derivatives such as lactose, sucrose, glucose, mannitol, or sorbitol; starch derivatives such as corn starch, potato starch, α-starch, or dextrin; cellulose derivatives such as microcrystalline cellulose; gum arabic; dextran; or pullulan; and inorganic fillers including silicic acid salt derivatives such as light anhydrous silicic acid, synthetic aluminum silicate, calcium silicate, or magnesium aluminometasilicate; phosphoric acid salts such as calcium hydrogen phosphate; carbonic acid salts such as calcium carbonate; or sulfuric acid salts such as calcium sulfate.

Examples of "lubricants" that may be used include stearic acid; stearic acid metal salts such as, calcium stearate or magnesium stearate; talc; colloidal silica; waxes such as beeswax or spermaceti; boric acid; adipic acid; sulfates such as sodium sulfate; glycol; fumaric acid; sodium stearyl fumarate; sodium benzoate; D,L-leucine; lauryl sulfates such as sodium lauryl sulfate or magnesium lauryl sulfate; silicic acids such as anhydrous silicic acid or silicic acid hydrate; or the starch derivatives described above.

Examples of "binders" that may be used include hydroxypropyl cellulose, hypromellose, polyvinylpyrrolidone, macrogol, or similar compounds as those of the fillers described above.

Examples of "disintegrants" that may be used include cellulose derivatives such as low-substituted hydroxypropyl cellulose, carboxymethyl cellulose, carboxymethyl cellulose calcium, or croscarmellose sodium; crospovidone; or chemically modified starches or celluloses such as carboxymethyl starch or carboxymethyl starch sodium.

Examples of "emulsifying agents" that may be used include colloidal clays such as bentonite or veegum; metal hydrides such as magnesium hydroxide or aluminum hydroxide; anionic surfactants such as sodium lauryl sulfate or calcium stearate; cationic surfactants such as benzalkonium chloride; or nonionic surfactants such as polyoxyethylene alkyl ethers, polyoxyethylene sorbitan fatty acid esters, or sucrose fatty acid esters.

Examples of "stabilizers" that may be used include parahydroxybenozoic acid esters such as methylparaben or propylparaben; alcohols such as chlorobutanol, benzyl alcohol, or phenyl ethyl alcohol; benzalkonium chloride; phenols such as phenol or cresol; thimerosal; dehydroacetic acid; or sorbic acid.

Examples of "sweetening and flavoring agents" that may be used include sweetening agents such as saccharin sodium or aspartame; acidulants such as citric acid, malic acid, or tartaric acid; and flavoring agents such as menthol, lemon, or orange.

Examples of "diluents" that may be used include lactose, mannitol, glucose, sucrose, calcium sulfate, calcium phosphate, hydroxypropyl cellulose, microcrystalline cellulose, water, ethanol, polyethylene glycol, propylene glycol, glycerol, starch, polyvinylpyrrolidone, magnesium aluminometasilicate, or mixtures thereof.

In the pharmaceutical composition of the present invention, (A) olmesartan medoxomil, (B), amlodipine, and (C) the calcium-containing excipient may be separate formulations or may be a combination product in which they are uniformly mixed (single formulation). Also in cases in which hydrochlorothiazide is further included in the pharmaceutical composition of the present invention, they may be separate formulations or a combination drug product in which they are uniformly mixed (single formulation), although the composition is preferably a combination product.

The pharmaceutical composition of the present invention is preferably a solid dosage form, examples of which include tablets (including sublingual tablets and orally disintegrating tablets), capsules (including soft capsules and microcapsules), granules, fine granules, powder, pills, chewable drugs, and troches. It is preferably a powder, fine granules, a granule, a capsule, or a tablet, more preferably a tablet, and even more preferably a tablet in which (A), (B), and (C) are uniformly combined. It is most preferably a tablet in which (A), (B), (C), and hydrochlorothiazide are uniformly combined.

There are no special restrictions regarding the manufacturing method of the drug product of the present invention as long as it is manufactured using a general method described in publications such as The Theory and Practice of Industrial Pharmacy (Third Edition) (Leon Lachman et al.: LEA&FEBIGER 1986) or Pharmaceutical Dosage Forms Tablets volume 1 (Second Edition) (Herbert A. Lieberman et al.: MARCEL DEKKER INC. 1989).

A tablet of the present invention is obtained, for example, by granulating, drying, and screening the main drugs together with a filler, a binder, a disintegrant or the like, adding and mixing a lubricant or the like, and compacting it into a tablet, according to commonly known methods. Here, granulation can be performed by means of wet granulation, dry granulation, or hot melt granulation; specifically, it is performed using a high-shear granulator, a fluid bed granulator, an extruder, or a roller compactor. After granulation, operations such as drying and screening may be performed as necessary. The mixture of the main drugs and a filler, a binder, a disintegrant, a lubricant, or the like may also be tableted directly. In addition, the tablet of the present invention may be provided with at least one layer of a film coating.

Coating is performed using a film coating machine, for example, and examples of film coating agents include sugar-coating agent, aqueous film coating agent, enteric film coating agent, and sustained release film coating agent.

Sucrose is used as a sugar-coating agent, and one or more types selected from talc, precipitated calcium carbonate, calcium phosphate, calcium sulfate, gelatin, gum arabic, polyvinylpyrrolidone, pullulan, and the like may also be used in combination.

Examples of aqueous film coating agents include cellulose derivatives such as hydroxypropyl cellulose, hypromellose, hydroxyethyl cellulose, methyl hydroxyethyl cellulose, and sodium carboxymethylcellulose; synthetic polymers such as polyvinylacetal diethylaminoacetate, aminoalkylmethacrylate copolymers, polyvinylpyrrolidone, polyvinyl alcohol, and polyvinyl alcohol copolymers; and polysaccharides such as pullulan.

Examples of enteric film coating agents include cellulose derivatives such as hydroxypropyl methyl cellulose phthalate, hydroxypropyl methyl cellulose acetate succinate, carboxymethyl ethyl cellulose, and cellulose acetate phthalate; acrylic acid derivatives such as methacrylic acid copolymer L, methacrylic acid copolymer LD, and methacrylic acid copolymer S; and natural substances such as shellac.

Examples of sustained release film coating agents include cellulose derivatives such as ethyl cellulose; and acrylic acid derivatives such as aminoalkyl methacrylate copolymer RS or an ethyl acrylate/methyl methacrylate/copolymer dispersion.

Two or more types of the coating agents described above may also be mixed at an appropriate ratio and used. In addition, appropriate pharmacologically acceptable excipients such as plasticizers, fillers, lubricants, masking agents, colorants, and preservatives may also be included as necessary.

The dissolution properties of the pharmaceutical composition of the present invention are measured in accordance with Dissolution Test method 2 (Paddle Method) of the General Tests, Processes and Apparatus of the Japanese Pharmacopoeia. For example, 900 mL of JP (Japanese Pharmacopoeia) $2^{nd}$ fluid for disintegration test (JP-2, pH 6.8) is used as a test solution at a paddle speed of 50 rpm, and the test solution is collected 30 minutes after the test is begun. This is filtered using a membrane filter with a pore size of 0.45 μm, and the dissolution rate of olmesartan medoxomil is calculated by assaying the filtrate using high-performance liquid chromatography.

The dose and dose ratio of olmesartan medoxomil and amlodipine, which are active ingredients of the pharmaceutical composition of the present invention, can be changed based on various conditions such as the activity of each drug and the patient's symptoms, age, and weight. The doses differ depending on factors such as symptoms and age, but if administered orally, they can be administered at a daily adult dose of 5-80 mg (preferably 10-40 mg) of olmesartan medoxomil and 2.5-20 mg (preferably 5-10 mg) of amlodipine (as free form base) 1-times per day (preferably once daily) based on the patient's symptoms. In cases in which hydrochlorothiazide is also included, the doses differ depending on factors such as symptoms and age, but if administered orally, they can be administered at a daily adult dose of 5-80 mg (preferably 10-40 mg) of olmesartan medoxomil, 2.5-20 mg (preferably 5-10 mg) of amlodipine (as free form base), and 5-50 mg (preferably 12.5-25 mg) of hydrochlorothiazide (as free form base) 1-6 times per day (preferably once daily) based on the patient's symptoms.

Although the ratio of the doses of olmesartan medoxomil and amlodipine, which are active ingredients of the pharmaceutical composition of the present invention, may also vary widely, the dose ratio of olmesartan medoxomil and amlodipine may be, for example, within the range of 1:50 to 50:1 (weight ratio) and is preferably within the range of 1:10 to 10:1. The most preferred mode is a tablet containing 40 mg/10 mg, 40 mg/5 mg, 20 mg/10 mg, 20 mg/5 mg, 10 mg/10 mg, or 10 mg/5 mg of olmesartan medoxomil/amlodipine. In cases in which hydrochlorothiazide is also included, the dose ratio of olmesartan medoxomil, amlodipine, and hydrochlorothiazide may be, for example, within the range of 1:50:1-50 to 50:1:1-50 (weight ratio) and is preferably within the range of 1:10:1-10 and 10:1:1-10. The most preferred mode is a tablet containing 40 mg/10 mg/12.5 mg, 40 mg/5 mg/12.5 mg, 40 mg/5 mg/25 mg, 40 mg/10 mg/25 mg, 20 mg/10 mg/12.5 mg, or 20 mg/5 mg/12.5 mg of olmesartan medoxomil/amlodipine/hydrochlorothiazide.

The pharmaceutical composition of the present invention is effective for the prevention or treatment of, for example, hypertension or diseases originating from hypertension (more specifically, hypertension, heart disease [angina pectoris, myocardial infarction, arrhythmia, heart failure, or cardiac hypertrophy], kidney disease [diabetic kidney disease, glomerular nephritis, or nephrosclerosis], or cerebrovascular disease [cerebral infarction or cerebral hemorrhage]).

EMBODIMENTS

The present invention will be described in further detail hereinafter by embodiments, but the present invention is not limited to these embodiments.

Embodiment 1

Drug Product Example 1

Manufacture of Drug Products Containing Either Olmesartan Medoxomil or Amlodipine Besylate or Both A filler (D-mannitol (made by Merck, Parteck M100)) and a disintegrant (carmellose (made by Gotoku Chemical Co., Ltd., NS-300)) were added to olmesartan medoxomil or amlodipine besylate or a combination of both, and in cases in which calcium was added, calcium carbonate was added and mixed using a pestle, in a mortar. After this was sieved, it was remixed, and a lubricant (magnesium stearate) was then added and mixed. The resulting mixture was compacted using a hydraulic press with a φ 9 mm convex with two radius punch, and tablets of formulations 1 through 6 (Table 1) were obtained.

Test Example 1

Dissolution Tests of Drug Products Containing Either Olmesartan Medoxomil or Amlodipine Besylate or Both One tablet was placed in 900 mL of JP $2^{nd}$ fluid for disintegration test (prepared by dissolving 40.83 g of potassium dihydrogen phosphate and 5.6 g of sodium hydroxide in 6 L of purified water), and dissolution tests were performed under the following conditions.

[Dissolution Test Conditions]
Dissolution medium: JP $2^{nd}$ fluid for disintegration test
Volume of dissolution medium: 900 mL
Temperature of dissolution medium: 37° C.
Test method: JP paddle method
Paddle speed: 50 rpm Thirty minutes after the test was begun, the test solution was sampled and filtered using a Mirex-LH (PTFE membrane, 0.45 μm, made by the Millipore Co.). Two mL from the initial stage was discarded, and the next 10 mL was collected in a test tube. This was transferred to a volumetric flask in which 2 mL of an internal standard solution was placed in advance to form a total of 10 mL, and this was used as a measurement specimen.

Assay was performed using HPLC under the following conditions.

[HPLC Conditions]
Analysis column: Waters Symmetry C8 (4.6 mm×100 mm, 3.5 μm, made by the Waters Co.)
Mobile phase: Mixture of a 0.25% phosphoric acid aqueous solution and acetonitrile (31:9)
Flow rate: Approximately 0.6 mL/min
Column temperature: 40° C.
Injection volume: 10 μL
Detector: Ultraviolet absorption spectrometer (measurement wavelength: 250 nm)

The following solutions were used as an internal standard solution and a standard solution.

Internal standard solution: 35 mg of 3-hydroxybenzoic acid methyl ester and 6 g of a phosphoric acid aqueous solution (0.25% w/v) were placed in a 500 mL volumetric flask and dissolved with an acetonitrile/purified water mixture (3/2) to form 500 mL.

Standard solution: 160 mg of olmesartan medoxomil, 56 mg of amlodipine besylate, and 100 mg of hydrochlorothiazide were weighed and dissolved in 200 mL of an acetonitrile/purified water mixture (3/2). Five mL of this solution was collected with a volumetric pipette, and after 20 mL of the internal standard solution was added, it was diluted to 100 mL with purified water.

The results of dissolution tests performed on drug products with combinations of olmesartan medoxomil and amlodipine besylate are shown in Table 2.

The dissolution percent of olmesartan medoxomil was low in drug products combined with amlodipine besylate, but the dissolution percent of olmesartan medoxomil recovered when calcium was added to the drug products.

Embodiment 2

Drug Product Example 2

Manufacture of Drug Products Containing Olmesartan Medoxomil, Amlodipine Besylate, and Hydrochlorothiazide (1)

A filler (D-mannitol (made by Merck, Parteck M100)), a disintegrant (carmellose calcium (made by Gotoku Chemical Co., Ltd., ECG-505) carmellose (made by Gotoku Chemical Co., Ltd., NS-300)), low-substituted hydroxypropyl cellulose (L-HPC) (made by Shin-Etsu Chemical Co., Ltd., LH-21), croscarmellose sodium (made by FMC Biopolymer, Ac-Di-Sol), carboxymethyl starch sodium (made by JRS Pharma, Explotab), and crospovidone (made by BASF, Kollidon CL) were added to olmesartan medoxomil, amlodipine besylate, and hydrochlorothiazide and mixed using a pestle, in a mortar. After this was sieved, it was remixed, and a lubricant (magnesium stearate) was then added and mixed. The resulting mixture was compacted using a hydraulic press, and tablets of formulations 7 through 13 (Table 3) were obtained.

Test Example 2

Dissolution Tests of Drug Products Containing Olmesartan Medoxomil, Amlodipine Besylate, and Hydrochlorothiazide (1)

Tests were performed using the same method as in (Test Example 1).

The results of dissolution tests performed on olmesartan medoxomil in formulations 7 through 13 are shown in Table 4.

As shown in Table 4, the dissolution of olmesartan medoxomil was favorable in the drug products containing carmellose calcium as a disintegrant (formulations 8 and 13).

Embodiment 3

Drug Product Example 3

Manufacture of Drug Products Containing Olmesartan Medoxomil, Amlodipine Besylate, and Hydrochlorothiazide (2)

A filler (D-mannitol (made by Merck, Parteck M100)), a disintegrant (carmellose (made by Gotoku Chemical Co., Ltd., NS-300)), and a partially pregelatinized starch (made by Colorcon, Starch1500) were added to olmesartan medoxomil, amlodipine besylate, and hydrochlorothiazide and mixed using a pestle, in a mortar. After this was sieved, it was remixed, and a lubricant (magnesium stearate) was then added and mixed. The resulting mixture was compacted using a hydraulic press with a φ 9 mm convex with two radius punch, and tablets of formulation 14 and 15 (Table 5) were obtained.

Test Example 3

Dissolution Tests of Drug Products Containing Olmesartan Medoxomil, Amlodipine Besylate, and Hydrochlorothiazide (2)

Tests were performed with the same method as in (Test Example 1) using JP $2^{nd}$ fluid for disintegration test and solutions prepared by dissolving 3, 30, and 60 mg of calcium chloride in 900 mL of JP $2^{nd}$ fluid for disintegration test as test solutions. Formulations 14 and 15 were used as test formulation.

The results of dissolution tests performed on olmesartan medoxomil in formulations 14 and 15 in the test solutions at each calcium concentration are shown in Table 6. The dissolution percent of olmesartan medoxomil was higher in the cases in which calcium was added to the test solutions than in the cases in which calcium was not added. Moreover, the dissolution percent of olmesartan medoxomil was always higher in the cases in which calcium was added to the test solutions, regardless of the amount of calcium added.

Embodiment 4

Drug Product Example 4

Manufacture of Drug Products Containing Olmesartan Medoxomil, Amlodipine Besylate, and Hydrochlorothiazide (3)

A filler (D-mannitol (made by Merck, Parteck M100)) and a disintegrant (carmellose calcium (made by Gotoku Chemical Co., Ltd., ECG-505)) were added to olmesartan medoxomil, amlodipine besylate, and hydrochlorothiazide and mixed for 15 min with a container blender. After this was sieved with a screening mill, it was remixed for 15 min with a container blender to obtain a mixed powder. After a lubricant (magnesium stearate) was added to the mixed powder and mixed with the container blender for 10 min, it was compacted at a pressure of 13 kN with a φ 9 mm convex with two radius punch so that the mass of the tablet was 300 mg using a rotary tableting machine, and tablets of formulations 16 through 19 (Table 7) were obtained.

Dissolution Tests of Drug Products Containing Olmesartan Medoxomil, Amlodipine Besylate, and Hydrochlorothiazide (3)

Tests were performed using the same method as in (Test Example 1).

The results of dissolution tests performed on olmesartan medoxomil in drug products with different amounts of carmellose calcium present are shown in Table 8. These formulations demonstrated higher olmesartan medoxomil dissolution percent at each quantity of carmellose calcium than the drug products of Embodiment 2 containing no carmellose calcium (formulations 7, 9, 10, 11, and 12).

Embodiment 5

Drug Product Example 5

Manufacture of Drug Products Containing Olmesartan Medoxomil, Amlodipine Besylate, and Hydrochlorothiazide (4-1)

A filler (D-mannitol (made by Merck, Parteck M100)), a disintegrant (carmellose (made by Gotoku Chemical Co., Ltd., NS-300)) and calcium-containing excipients (calcium silicate, calcium hydrogen phosphate, calcium carbonate, calcium sulfate dihydrate, calcium ascorbate, and calcium chloride) were added to olmesartan medoxomil, amlodipine besylate, and hydrochlorothiazide and mixed using a pestle, in a mortar. After this was sieved, it was remixed, and a lubricant (magnesium stearate and calcium stearate) was then added and mixed. The resulting mixture was compacted using a hydraulic press with a φ 9 mm convex with two radius punch, and tablets of formulations 20 through 27 (Table 9) were obtained.

Reference Example 1

Manufacture of Drug Products Containing Olmesartan Medoxomil, Amlodipine Besylate, and Hydrochlorothiazide (4-2)

A filler (D-mannitol (made by Merck, Parteck M100)), a disintegrant (carmellose (made by Gotoku Chemical Co., Ltd., NS-300)) and magnesium-containing excipients (magnesium aluminometasilicate, magnesium hydroxide, magnesium oxide, and magnesium carbonate) were added to olmesartan medoxomil, amlodipine besylate, and hydrochlorothiazide and mixed using a pestle, in a mortar. After this was sieved, it was remixed, and lubricants (magnesium stearate and calcium stearate) were then added and mixed. The resulting mixture was compacted using a hydraulic press with a φ 9 mm convex with two radius punch, and tablets of formulations 28 through 31 (Table 10) were obtained.

Test Example 5

Dissolution Tests of Drug Products Containing Olmesartan Medoxomil, Amlodipine Besylate, and Hydrochlorothiazide (4)

Tests were performed using the same method as in (Test Example 1).

The results of dissolution tests performed on olmesartan medoxomil in formulations with various calcium-containing excipients within the normally used range are shown in Table 11. All of the drug products demonstrated higher dissolution percent than that of formulation 20, which does not contain calcium. Moreover, as a reference example shown in Table 12, among formulations containing magnesium as an alkali earth metal, those containing magnesium aluminometasilicate or magnesium carbonate demonstrated a high dissolution percent, but the dissolution percents were low in the formulations with other magnesium-containing excipients.

Embodiment 6

Drug Product Example 6

Manufacture of Drug Products Containing Olmesartan Medoxomil, Amlodipine Besylate, and Hydrochlorothiazide (5)

A filler (D-mannitol (made by Merck, Parteck M100)), a disintegrant (partially pregelatinized starch (made by Colorcon, Starch1500)), low-substituted hydroxypropyl cellulose (L-HPC) (made by Shin-Etsu Chemical Co., Ltd., LH-21), croscarmellose sodium (made by FMC Biopolymer, Ac-Di-Sol), and carboxymethyl starch sodium (made by JRS Pharma, Explotab) were added to olmesartan medoxomil, amlodipine besylate, and hydrochlorothiazide and mixed using a pestle, in a mortar after adding calcium carbonate as a calcium excipient. After this was sieved, it was remixed, and a lubricant (magnesium stearate) was then added and mixed. The resulting mixture was compacted using a hydraulic press with a φ 9 mm convex with two radius punch, and tablets of formulations 32 through 39 (Table 13) were obtained.

Test Example 6

Dissolution Tests of Drug Products Containing Olmesartan Medoxomil, Amlodipine Besylate, and Hydrochlorothiazide (5)

Tests were performed using the same method as in (Test Example 1).

The results of dissolution tests performed on olmesartan medoxomil in formulations 32 through 39 are shown in Table 14. As shown in Table 14, in cases in which the same disintegrants were added, the dissolution percents of olmesartan medoxomil were higher in formulations with calcium-containing excipients than in drug products without calcium-containing excipients.

Tests were performed on three tablets, and the mean values are shown.

TABLE 1

| Ingredient | Composition per tablet (mg) | | | | | |
|---|---|---|---|---|---|---|
| | Formulation 1 | Formulation 2 | Formulation 3 | Formulation 4 | Formulation 5 | Formulation 6 |
| Olmesartan medoxomil | 40 | — | 40 | 40 | — | 40 |
| Amlodipine besylate | — | 13.888 | 13.888 | — | 13.888 | 13.888 |
| D-mannitol | 196.4 | 222.512 | 182.512 | 166.4 | 192.512 | 152.512 |
| Carmellose | 60 | 60 | 60 | 60 | 60 | 60 |
| Calcium carbonate | — | — | — | 30 | 30 | 30 |
| Magnesium stearate | 3.6 | 3.6 | 3.6 | 3.6 | 3.6 | 3.6 |
| Total | 300 | 300 | 300 | 300 | 300 | 300 |

TABLE 2

| | Formulation 1 | Formulation 2 | Formulation 3 | Formulation 4 | Formulation 5 | Formulation 6 |
|---|---|---|---|---|---|---|
| Olmesartan medoxomil dissolution rate (%) | 95.2 | — | 64.5 | 87.7 | — | 90.0 |
| Amlodipine besylate dissolution rate (%) | — | 82.5 | 90.8 | — | 95.1 | 96.5 |

TABLE 3

| Ingredient | Composition per tablet (mg) | | | | | | |
|---|---|---|---|---|---|---|---|
| | Formulation 7 | Formulation 8 | Formulation 9 | Formulation 10 | Formulation 11 | Formulation 12 | Formulation 13 |
| Olmesartan medoxomil | 40 | 40 | 40 | 40 | 40 | 40 | 40 |
| Amlodipine besylate | 13.888 | 13.888 | 13.888 | 13.888 | 13.888 | 13.888 | 13.888 |
| Hydrochlorothiazide | 25 | 25 | 25 | 25 | 25 | 25 | 25 |
| D-mannitol | 250.812 | 250.812 | 250.812 | 313.812 | 313.812 | 313.812 | 156.612 |
| L-HPC | 84 | — | — | — | — | — | — |
| Carmellose calcium | — | 84 | — | — | — | — | 60 |
| Carmellose | — | — | 84 | — | — | — | — |
| Croscarmellose sodium | — | — | — | 21 | — | — | — |
| Carboxymethyl starch sodium | — | — | — | — | 21 | — | — |
| Crospovidon | — | — | — | — | — | 21 | — |
| Magnesium stearate | 6.3 | 6.3 | 6.3 | 6.3 | 6.3 | 6.3 | 4.5 |
| Total | 420 | 420 | 420 | 420 | 420 | 420 | 300 |

TABLE 4

| | Formulation 7 | Formulation 8 | Formulation 9 | Formulation 10 | Formulation 11 | Formulation 12 | Formulation 13 |
|---|---|---|---|---|---|---|---|
| Olmesartan medoxomil dissolution rate (%) | 60.9 | 89.6 | 58.9 | 45.3 | 40.3 | 44.0 | 89.8 |

TABLE 5

| Ingredient | Composition per tablet (mg) | |
|---|---|---|
| | Formulation 14 | Formulation 15 |
| Olmesartan medoxomil | 40 | 40 |
| Amlodipine besylate | 13.888 | 13.888 |
| Hydrochlorothiazide | 25 | 25 |
| D-mannitol | 157.512 | 112.512 |
| Carmellose | 60 | — |
| Partially pregelatinized starch | — | 105 |
| Magnesium stearate | 3.6 | 3.6 |
| Total | 300 | 300 |

TABLE 6

| Formulation | Composition of calcium chloride added to 900 mL of JP 2$^{nd}$ fluid for disintegration test (mg) | | | |
|---|---|---|---|---|
| | 0 | 3 | 30 | 60 |
| Olmesartan medoxomil dissolution rate (%) Formulation 14 | 66.2 | 87.6 | 81.2 | 85.4 |
| Olmesartan medoxomil dissolution rate (%) Formulation 15 | 67.7 | 90.7 | 89.8 | 89.5 |

TABLE 7

| Ingredient | Composition per tablet (mg) | | | |
|---|---|---|---|---|
| | Formulation 16 | Formulation 17 | Formulation 18 | Formulation 19 |
| Olmesartan medoxomil | 40 | 40 | 40 | 40 |
| Amlodipine besylate | 13.888 | 13.888 | 13.888 | 13.888 |
| Hydrochlorothiazide | 25 | 25 | 25 | 25 |
| D-mannitol | 201.612 | 195.612 | 186.612 | 171.612 |
| Carmellose calcium | 15 | 21 | 30 | 45 |
| Magnesium stearate | 4.5 | 4.5 | 4.5 | 4.5 |
| Total | 300 | 300 | 300 | 300 |

TABLE 8

| | Formulation 16 | Formulation 17 | Formulation 18 | Formulation 19 |
|---|---|---|---|---|
| Olmesartan medoxomil dissolution rate (%) | 84.9 | 87.1 | 89.7 | 91.9 |

TABLE 9

| Ingredient | Composition per tablet (mg) | | | | | | | |
|---|---|---|---|---|---|---|---|---|
| | Formulation 20 | Formulation 21 | Formulation 22 | Formulation 23 | Formulation 24 | Formulation 25 | Formulation 26 | Formulation 27 |
| Olmesartan medoxomil | 40 | 40 | 40 | 40 | 40 | 40 | 40 | 40 |
| Amlodipine besylate | 13.888 | 13.888 | 13.888 | 13.888 | 13.888 | 13.888 | 13.888 | 13.888 |
| Hydrochlorothiazide | 25 | 25 | 25 | 25 | 25 | 25 | 25 | 25 |
| D-mannitol | 157.512 | 127.512 | 127.512 | 127.512 | 127.512 | 157.512 | 127.512 | 127.512 |
| Carmellose | 60 | 60 | 60 | 60 | 60 | 60 | 60 | 60 |
| Calcium silicate | — | 30 | — | — | — | — | — | — |
| Calcium hydrogen phosphate | — | — | 30 | — | — | — | — | — |
| Calcium carbonate | — | — | — | 30 | — | — | — | — |
| Calcium sulfate dihydrate | — | — | — | — | 30 | — | — | — |
| Calcium ascorbate | — | — | — | — | — | — | 30 | — |
| Calcium chloride | — | — | — | — | — | — | — | 30 |
| Magnesium stearate | 3.6 | 3.6 | 3.6 | 3.6 | 3.6 | — | 3.6 | 3.6 |
| Calcium stearate | — | — | — | — | — | 3.6 | — | — |
| Total | 300 | 300 | 300 | 300 | 300 | 300 | 300 | 300 |

TABLE 10

| Ingredient | Composition per tablet (mg) | | | |
|---|---|---|---|---|
| | Formulation 28 | Formulation 29 | Formulation 30 | Formulation 31 |
| Olmesartan medoxomil | 40 | 40 | 40 | 40 |
| Amlodipine besylate | 13.888 | 13.888 | 13.888 | 13.888 |
| Hydrochlorothiazide | 25 | 25 | 25 | 25 |
| D-mannitol | 127.512 | 127.512 | 127.512 | 127.512 |
| Carmellose | 60 | 60 | 60 | 60 |
| Magnesium aluminometasilicate | 30 | — | — | — |
| Magnesium hydroxide | — | 30 | — | — |
| Magnesium oxide | — | — | 30 | — |
| Magnesium carbonate | — | — | — | 30 |
| Magnesium stearate | 3.6 | 3.6 | 3.6 | 3.6 |
| Total | 300 | 300 | 300 | 300 |

TABLE 11

| | Formulation 20 | Formulation 21 | Formulation 22 | Formulation 23 | Formulation 24 | Formulation 25 | Formulation 26 | Formulation 27 |
|---|---|---|---|---|---|---|---|---|
| Olmesartan medoxomil dissolution rate (%) | 66.2 | 91.4 | 72.7 | 88.8 | 76.1 | 77.6 | 90.6 | 85.1 |

TABLE 12

|  | Formulation 28 | Formulation 29 | Formulation 30 | Formulation 31 |
|---|---|---|---|---|
| Olmesartan medoxomil dissolution rate (%) | 80.2 | 52.0 | 61.7 | 73.8 |

TABLE 13

| | Composition per tablet (mg) | | | | | | | |
|---|---|---|---|---|---|---|---|---|
| Ingredient | Formulation 32 | Formulation 33 | Formulation 34 | Formulation 35 | Formulation 36 | Formulation 37 | Formulation 38 | Formulation 39 |
| Olmesartan medoxomil | 40 | 40 | 40 | 40 | 40 | 40 | 40 | 40 |
| Amlodipine besylate | 13.888 | 13.888 | 13.888 | 13.888 | 13.888 | 13.888 | 13.888 | 13.888 |
| Hydrochloro thiazide | 25 | 25 | 25 | 25 | 25 | 25 | 25 | 25 |
| D-mannitol | 112.512 | 202.512 | 157.512 | 202.512 | 82.512 | 172.512 | 127.512 | 172.512 |
| Partially pregelatinized starch | 105 | — | — | — | 105 | — | — | — |
| Carboxymethyl starch sodium | — | 15 | — | — | — | 15 | — | — |
| L-HPC | — | — | 60 | — | — | — | 60 | — |
| Croscarmellose sodium | — | — | — | 15 | — | — | — | 15 |
| Calcium carbonate | — | — | — | — | 30 | 30 | 30 | 30 |
| Magnesium stearate | 3.6 | 3.6 | 3.6 | 3.6 | 3.6 | 3.6 | 3.6 | 3.6 |
| Total | 300 | 300 | 300 | 300 | 300 | 300 | 300 | 300 |

TABLE 14

| | Formulation 32 | Formulation 33 | Formulation 34 | Formulation 35 | Formulation 36 | Formulation 37 | Formulation 38 | Formulation 39 |
|---|---|---|---|---|---|---|---|---|
| Olmesartan medoxomil dissolution rate (%) | 67.7 | 55.1 | 63.1 | 58.9 | 90.3 | 68.2 | 82.7 | 82.7 |

FIELD OF INDUSTRIAL APPLICATION

With the present invention, a pharmaceutical composition with improved dissolution properties containing (A) olmesartan medoxomil and (B) amlodipine as active ingredients and (C) a calcium-containing excipient can be obtained.

The invention claimed is:

1. A pharmaceutical tablet consisting of (A) olmesartan medoxomil, (B) amlodipine besylate and (C) hydrochlorothiazide as the only active drug ingredients and (D) one or more pharmaceutically acceptable calcium-containing excipients selected from the group consisting of carmellose calcium, calcium silicate, calcium carbonate, calcium ascorbate and calcium chloride, wherein said calcium-containing excipient is in an amount of from 5 to 20 weight percent of said pharmaceutical tablet and wherein said tablet is prepared by direct tableting.

2. The pharmaceutical tablet according to claim 1, wherein said calcium-containing excipient is carmellose calcium.

3. The pharmaceutical tablet according to claim 1 which is coated.

4. The pharmaceutical tablet according to claim 3, wherein said calcium-containing excipient is included in the coating.

5. A method for treating or preventing hypertension comprising administering the pharmaceutical tablet according to claim 1 to a patient.

6. The pharmaceutical tablet according to claim 1, wherein said calcium-containing excipient in said pharmaceutical composition is in an amount of 10 weight percent of said pharmaceutical composition.

7. The pharmaceutical tablet according to claim 2, wherein said calcium-containing excipient in said pharmaceutical composition is in an amount of 10 weight percent of said pharmaceutical composition.

8. The pharmaceutical tablet according to claim 1, wherein olmesartan medoxomil is in an amount of 10 to 40 mg, amlodipine besylate is in an amount of 5 to 10 mg based on a free form base and hydrochlorothiazide is in an amount of 12.5 to 25 mg based on a free form base.

* * * * *